United States Patent [19]

Shean et al.

[11] 4,303,582
[45] Dec. 1, 1981

[54] SPRAY DRYING PROCESS FOR PREPARATION OF SOLID SODIUM AMOXYCILLIN

[75] Inventors: David H. S. Shean, Cranleigh; John R. Steel, Newdigate, both of England

[73] Assignee: Beecham Group Limited, England

[21] Appl. No.: 152,711

[22] Filed: May 23, 1980

Related U.S. Application Data

[63] Continuation of Ser. No. 962,196, Nov. 20, 1978, abandoned, which is a continuation of Ser. No. 887,837, Mar. 7, 1978, abandoned, which is a continuation of Ser. No. 822,259, Aug. 5, 1977, abandoned.

[30] Foreign Application Priority Data

Aug. 10, 1976 [GB] United Kingdom ............... 33176/76

[51] Int. Cl.$^3$ ............................................ C07D 499/18
[52] U.S. Cl. ..................................... 260/239.1; 424/71
[58] Field of Search ...................... 260/239.1; 424/271

[56] References Cited

U.S. PATENT DOCUMENTS 3,674,776  7/1972  Long et al. ...................... 260/239.1
4,029,804  6/1977  Clark et al. .......................... 424/271

OTHER PUBLICATIONS

Kirk–Othmer, "Encyclopedia of Chemical Technology", vol. 7, 2nd Ed. pp. 368–369, (1965).
Remington's, "Pharmaceutical Sciences", 13th Ed, pp. 179–180, (1965).

Primary Examiner—Natalie Trousof
Assistant Examiner—Vera C. Clarke
Attorney, Agent, or Firm—Jacobs & Jacobs

[57] ABSTRACT

Sodium amoxycillin is obtained by spray drying a solution of sodium amoxycillin in aqueous isopropyl alcohol, wherein the initial ratio of isopropyl alcohol to sodium amoxycillin present in the solution to be spray dried is from 5:3 to 3:1 w/w.

3 Claims, No Drawings

SPRAY DRYING PROCESS FOR PREPARATION OF SOLID SODIUM AMOXYCILLIN

This is a continuation of Ser. No. 962,196, filed Nov. 20, 1978, which is a continuation of Ser. No. 887,837, filed Mar. 7, 1978, which is a continuation of Ser. No. 822,259, filed Aug. 5, 1977, all now abandoned.

The present invention relates to a process for the preparation of sodium amoxycillin, to the sodium amoxycillin so prepared and to the solutions used in the process.

British Patent Specification No. 1,241,844 discloses inter alia amoxycillin and its salts. Amoxycillin, which is the penicillin of the formula:

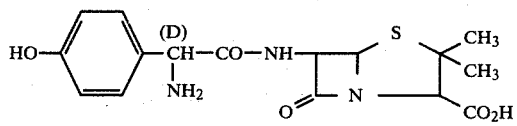

is widely recognised as having a broad spectrum of antibacterial activity of a high order. One of amoxycillin's great advantages is that it is very well absorbed after oral administration but there are occasions when it is desirable to administer it parenterally. It is possible to use the methods disclosed in British Patent Specification No. 1,241,844 to prepare sodium amoxycillin which may then be dissolved in sterile, pyrogen-free water and used as an injectable composition. However, the previously disclosed process for the preparation of sodium amoxycillin tends to give somewhat poor results in terms of yield and purity, for example due to contamination by penicilloic acid or dimers. These disadvantages have not prevented the use of the known process for preparing the salt for use in injectable compositions but clearly it would be advantageous to have a process available that led to good yields of a purer product that has improved stability and appearance on reconstitution. Such an improved process has now been discovered.

Accordingly the present invention provides a process for the preparation of solid sodium amoxycillin which process comprises spray drying a solution of sodium amoxycillin in aqueous isopropyl alcohol.

The concentration of sodium amoxycillin in the solution to be spray dried will normally be in the range 5–25% w/w, more usually 7–20% w/w and more suitably 8–16% w/w, for example about 15% w/w.

The ratio of isopropanol to sodium amoxycillin present in the solution to be spray dried will normally be from 5:3 to 3:3 w/w, and will preferably be about 4:3 w/w as this ratio gives a particularly acceptable product.

The ratio of isopropanol to water in the solution to be spray dried is relatively unimportant as long as it allows a homogeneous solution to be formed as we believe it is the ratio of sodium amoxycillin to isopropanol that produces the beneficial stability encountered. However we have found that 10–20% w/w of isopropanol in the solution to be spray dried is acceptable and about 12–17%, for example about 15% to be preferred.

The operation of the spray dryer will occur under conventional non-forcing conditions. Thus for example excessive temperatures that are unsuitable for the preparation of pharmaceutical agents such as penicillin salts will be avoided. Similarly the spray dryer will be operated to remove substantially all the solvent as is normal. Such procedures are routine for those familiar with the techniques of spray drying. Normally the desired results are obtained by operating the spray dryer with an inlet temperature within the range 155°–200° C. and with an outlet temperature within the range 95°–110° C., e.g. 95°–100° C. The throughput rate is chosen so that the resulting sodium amoxycillin is produced as a dry powder. This is normally achieved by operating the spray dryer under conditions of throughput that result in the total operation being complete in not more than 1 hour. The retention time in the drying cavity is generally in the order of 1 to 2 seconds. The solution to be dried may be atomised within the dryer by an atomising nozzle or by a centrifugal disc but in general we have preferred to use a centrifugal disc operated at a speed that produces a spray having a surface area in the order of 1000 square meters per liter to allow rapid drying in conventional manner. The dryer is operated to produce a final dried powder containing not more than 1.5% of isopropanol and preferably 0.1 to 1.0% w/w isopropanol, for example 0.2 to 0.8% w/w isopropanol. Operation in this manner thereby results in the material containing less than 3% w/w water, usually 0.4 to 2.8% water, for example 0.5 to 2.5% water.

The sodium amoxycillin produced by this process has the advantage of containing low levels of impurities such as its penicilloate or dimer. Furthermore the product may be reconstituted in water to yield a solution that has better stability and appearance than that obtained by dissolving previously known forms of sodium amoxycillin in water. These surprising advantages allow the product to be reconstituted for use in water or saline and thereby avoids the inconvenient necessity to reconstitute in aqueous ethanol or the like as described in British Pat. No. 1,463,563.

The solution to be spray dried may be prepared by suspending substantially pure amoxycillin trihydrate (preferably at least 97% pure) in a mixture of water and isopropanol and adding thereto an aqueous solution of sodium hydroxide until dissolution is complete but avoiding any major excess of base.

Suitably the concentration of the sodium hydroxide solution used is from 0.5 to 4 N, more suitably 1 to 3 N, for example about 2 N.

The solution of sodium hydroxide should be added to the suspension at such a rate that high pH levels (as measured on conventional pH meters) are avoided, for example a gradual addition that avoids pH values greater than 10 at 15°–35° C. may be employed. More suitably the rate is such that the pH does not exceed 9.8. The final observed pH of the solution should be above 8.5 and more suitably above 9, for example about 9.5. Addition of the sodium hydroxide solution may conveniently take place in the range 15°–35° C. but temperatures of about 20°–30° C. are more suitable, for example about 25° C. Most suitably addition is accompanied by agitation to aid in the formation of a homogeneous mixture useful in avoiding localised pH anomalies. Generally from 1.02 to 1.12 equivalents of sodium hydroxide are sufficient to achieve dissolution of the amoxycillin but more suitably 1.08 to 1.11 equivalents, and preferably 1.10 equivalents of sodium hydroxide are employed.

If desired a solution of sodium isopropoxide in isopropanol may be used instead of the sodium hydroxide solution but we prefer to use sodium hydroxide.

After dissolution of the amoxycillin trihydrate the solution should be chilled for example to about 5° C. to −10° C. and more suitably to about 0° C. Prior to spray drying the solution should be filtered to remove any particulate (that is solid) matter.

The solid sodium amoxycillin produced by the process of this invention will not normally contain more than 6% w/w of degradation products such as penicilloate or dimer, for example it will usually contain less than 5% and more suitably less than 4% of such material. Operation of the process will however generally produce some small quantities of such degradation materials, for example at least 2% of penicilloate and dimer generally occurs.

Operation of the process of this invention leads to an advantageously pure form of solid sodium amoxycillin which contains less than 1.5% w/w organic solvent (that is isopropyl alcohol) residue, for example 0.1 to 1.0% w/w and preferably 0.2 to 0.8% w/w and less than 3% w/w water, for example 0.5 to 2.5% w/w although 2.5 to 3% w/w is more easily achieved.

Residues of isopropanol and water greater than 1.5% and 3% respectively should be avoided as they tend to decrease the storage stability of the product. The preceding narrower ranges are preferred as they give rise to a product having improved characteristics.

The sodium amoxycillin of this invention may also contain small quantities of other impurities such as sodium chloride which are derived from impurities in the original amoxycillin trihydrate used in the process.

From the preceding it will be appreciated that the sodium amoxycillin produced by this process is of unusually high purity that is normally at least 85% w/w (absolute basis, i.e. sodium amoxycillin per se present in product) and more suitably 87–90% w/w.

In addition to the previously described advantages of stability to storage and stability and good appearance after reconstitution, the reconstituted sodium amoxycillin in a 10% solution normally has a pH of between 8.5 and 9.3 and more usually between 8.7 and 9.1 which aids patient acceptability.

This material may be used in reconstituted doses of for example about 0.25 g to 1.0 g by dissolving in sterile, pyrogen-free water in conventional manner. The powder for reconstitution may be kept sealed in vials, ampoules or the like in conventional manner.

The reconstituted solutions produce good peak blood levels after administration by injection. The sodium amoxycillin produced by the process of this invention has extremely low toxicity.

The following Examples illustrate the invention:

EXAMPLE 1

Preparation of Sodium Amoxycillin

Amoxycillin trihydrate (335 g) was suspended in a mixture of distilled pyrogen-free water (810 ml) and isopropanol (506 ml). The suspension was stirred vigorously while a solution of sodium hydroxide (2 N, 425 ml) was added over a period of 5 minutes. The addition was carried out at a temperature within the range 24°–30° C. The solution was then chilled rapidly to 0° C. and maintained at this temperature for 5 minutes and filtered. The clear filtrate was then sterile filtered. This solution was spray dried using an inlet temperature of 155°–200° C. and an outlet temperature of 95°–100° C.

Spray drying with a centrifugal disc ANHYDRO Laboratory Spray Dryer under these conditions at a feed rate of 3 liters per hour yielded 0.3 kg of spray dried sodium amoxycillin per hour.

The preceding process may also be employed with an inlet temperature of 195°–200° C. and an outlet temperature of 100°–150° C. A suitable disc speed is 45000 revs/min and a suitable air flow rate is 125 m³/hour.

The spray dried sodium amoxycillin produced by this process may be filled into vials and ampoules in conventional manner. Excess handling under wet atmospheres should be avoided. [ANHYDRO supplied by Anhydro AS, 2860 Soeborg, 8 Ostmarken, Copenhagen, Denmark].

EXAMPLE 2

Preparation of Sodium Amoxycillin

Clear filtrate as prepared by the method of Example 1 may be spray dried in a rotary disc 'NIRO Atomizer Production Minor Spray-Dryer' at a feed rate of 10 liters per hour yielding 1.2 kg per hour of spray dried sodium amoxycillin. With this machine an inlet temperature of 155°–165° C. and an outlet temperature of 105°–110° C. and atomiser 28000 revs per minute may be employed. (NIRO supplied by Niro Atomiser Ltd., 2860 Soeberg, 305 Gladsaxevej, Copenhagen, Denmark)

The average approximate specification of 40 batches of sodium amoxycillin produced by this process is as follows:

| | |
|---|---|
| Sodium amoxycillin | 89% |
| Water | 2.7% |
| Isopropyl alcohol | 0.7% |
| Penicilloate Dimer | 5.6% |

On reconstitution this material had a pH of 8.9 at 10% w/v. The solution appeared clear and colourless.

What we claim is:

1. A process for the preparation of solid sodium amoxycillin of improved stability and purity which comprises subjecting a solution consisting of from 5% to 25% by weight sodium amoxycillin in aqueous isopropanol wherein the initial weight ratio in the solution of isopropanol to sodium amoxycillin, which solution has been cooled to from 5° to −10° C., to spray drying at an inlet temperature of from 155° to 200° C. and an outlet temperature of from 95° to 110° C., with a retention time of from 1 to 2 seconds.

2. A process according to claim 1 wherein the isopropanol is a 12 to 17% by weight solution of isopropanol in water.

3. A process according to claim 2 wherein the aqueous isopropanol contains 15% by weight of isopropanol.

* * * * *

UNITED STATES PATENT AND TRADEMARK OFFICE
CERTIFICATE OF CORRECTION

PATENT NO. : 4,303,582
DATED : December 1, 1981
INVENTOR(S) : DAVID HORACE SHEAN ET AL.

It is certified that error appears in the above-identified patent and that said Letters Patent are hereby corrected as shown below:

Col. 4, line 51, after --amoxycillin" and before the comma insert --is from 5:3 to 3:3--.

Signed and Sealed this

Ninth Day of August 1983

[SEAL]

Attest:

GERALD J. MOSSINGHOFF

*Attesting Officer*   *Commissioner of Patents and Trademarks*